United States Patent
Jose et al.

(10) Patent No.: US 12,110,481 B2
(45) Date of Patent: Oct. 8, 2024

(54) METHOD AND SYSTEM FOR CREATING RECONFIGURABLE BIO-PROCESSING WORKFLOWS

(71) Applicant: Cytiva Sweden AB, Uppsala (SE)

(72) Inventors: Victor Jose, Bangalore (IN); Andreas Axen, Uppsala (SE); Klaus Gebauer, Uppsala (SE); Veena B N Rao, Bangalore (IN); Patric Fricking, Uppsala (SE); Hanish Lakhani, Bangalore (IN)

(73) Assignee: Cytiva Sweden AB, Uppsala (SE)

( * ) Notice: Subject to any disclaimer, the term of this patent is extended or adjusted under 35 U.S.C. 154(b) by 756 days.

(21) Appl. No.: 16/607,516

(22) PCT Filed: Apr. 18, 2018

(86) PCT No.: PCT/EP2018/059809
§ 371 (c)(1),
(2) Date: Oct. 23, 2019

(87) PCT Pub. No.: WO2018/197273
PCT Pub. Date: Nov. 1, 2018

(65) Prior Publication Data
US 2020/0131467 A1    Apr. 30, 2020

(30) Foreign Application Priority Data
Apr. 28, 2017   (IN) .............................. 201741015122

(51) Int. Cl.
*C12M 1/36*     (2006.01)
*C12M 1/00*     (2006.01)
*G16H 10/40*    (2018.01)

(52) U.S. Cl.
CPC ............ *C12M 41/48* (2013.01); *C12M 23/26* (2013.01); *C12M 23/28* (2013.01); *G16H 10/40* (2018.01)

(58) Field of Classification Search
CPC ....... G16H 10/40; C12M 41/48; C12M 23/28; C12M 23/26
See application file for complete search history.

(56) References Cited

U.S. PATENT DOCUMENTS

2004/0085562 A1   5/2004   Fromherz
2005/0254055 A1   11/2005  Peng
(Continued)

FOREIGN PATENT DOCUMENTS

CN       102656282 A      9/2012
CN       101331503 A      12/2012
(Continued)

OTHER PUBLICATIONS

International Search Report for PCT Application No. 2018/059810 mailed Jul. 19, 2018 (9 pages).
(Continued)

*Primary Examiner* — Shogo Sasaki
(74) *Attorney, Agent, or Firm* — Eversheds-Sutherland (US) LLP

(57) ABSTRACT

A bio-processing system (100) is presented. The bio-processing system (100) includes one or more bio-processing units (110-114), one or more process supporting devices (116, 118), one or more sensors (120-132), and a bio-processing workflow controller (104) wirelessly coupled to at least one of the one or more bio-processing units (110-114), the one or more process supporting devices (116, 118), and the one or more sensors (120-132). The bio-processing workflow controller (104) includes a processor (202) configured to create a reconfigurable bio-processing workflow, (Continued)

and where the reconfigurable bio-processing workflow is representative of an arrangement of one or more of the one or more bio-processing units (110-114), the one or more process supporting devices (116, 118), and the one or more sensors (120-32) to perform at least one bio-processing operation.

10 Claims, 5 Drawing Sheets

(56) References Cited

U.S. PATENT DOCUMENTS

| | | | |
|---|---|---|---|
| 2007/0243626 | A1* | 10/2007 | Windeyer .......... G01N 35/0092 |
| | | | 422/292 |
| 2008/0069739 | A1* | 3/2008 | Ludwig ................ B01J 19/0093 |
| | | | 422/50 |
| 2009/0176301 | A1 | 7/2009 | Oldenburg et al. |
| 2010/0144022 | A1 | 6/2010 | Surapaneni |
| 2012/0187897 | A1 | 7/2012 | Lenk et al. |
| 2013/0193774 | A1 | 8/2013 | Yang et al. |
| 2014/0175876 | A1 | 6/2014 | Cheatham, III et al. |
| 2014/0212954 | A1 | 7/2014 | Auner et al. |
| 2014/0255910 | A1 | 9/2014 | Arnold et al. |
| 2014/0287449 | A1 | 9/2014 | Bonyuet |
| 2015/0128733 | A1 | 5/2015 | Taylor et al. |
| 2015/0137992 | A1* | 5/2015 | Potyrailo ........... G01N 27/3272 |
| | | | 340/870.07 |
| 2017/0039441 | A1 | 2/2017 | Lim et al. |

FOREIGN PATENT DOCUMENTS

| | | |
|---|---|---|
| CN | 102859527 A | 1/2013 |
| CN | 105471123 A | 4/2016 |
| CN | 104769766 A | 4/2018 |
| EP | 2774979 A1 | 9/2014 |
| EP | 2822144 A1 | 1/2015 |
| JP | 2015123300 A | 7/2015 |
| WO | 2013/096842 A2 | 6/2013 |
| WO | 2016/037100 A1 | 3/2016 |

OTHER PUBLICATIONS

International Search Report for PCT Application No. 2018/059811 mailed Jul. 26, 2018 (8 pages).
PCT International Search Report and Written Opinion for PCT Application No. PCT/EP2018/059809 mailed Aug. 21, 2018 (11 pages).
Anonymous, "Wireless—Wikipedia", 2017, https://en.wikipedia.org/w/index.php?title=Wireless&oldid=772893211, 9 pages.
Anonymous, "Integrated Bioprocess Solutions," 2016, https://www.merckmillipore.com/INTERSHOP/web/WFS/Merck-CH-Site/de_DE/-/CHF/ShowDocument-Pronet?id=201605.055, 24 pages.
Anonymous, "BioProcess ProductGuide 2012/2013," 2012, http://legacy.gelifesciences.com/downloads/Download/29013303AB.pdf, 284 pages.
European Office Action for EP Application No. 18718446.0 mailed Nov. 30, 2020 (7 pages).
European Office Action for EP Application No. 18718447.8 mailed Dec. 2, 2020 (7 pages).
China National Intellectual Property Administration (CNIPA), First Office Action & Search Report for CN Application No. 20188027625.3 dated Feb. 2, 2023, (35 pages, including Reporting Letter and English translations).
China National Intellectual Property Administration (CNIPA), First Office Action & Search Report for CN Application No. 201880027789.6 dated Jan. 20, 2023, (36 pages including English translations).
U.S. Non Final Office Action for corresponding U.S. Appl. No. 16/605,115, mailed Apr. 28, 2023, 23 pages.

\* cited by examiner

METHOD AND SYSTEM FOR CREATING RECONFIGURABLE BIO-PROCESSING WORKFLOWS

CROSS REFERENCE TO RELATED APPLICATIONS

This application claims the priority benefit of PCT/EP2018/059809 filed on Apr. 18, 2018, which claims priority benefit of India Patent Application No. 201741015122 filed on Apr. 28, 2017, the entire contents of which are hereby incorporated by reference herein.

FIELD OF THE INVENTION

Embodiments of the present specification generally relate to a bio-processing system, and in particular to a method and a system for creating, monitoring and controlling a reconfigurable bio-processing workflow.

BACKGROUND

Typically, bio-processing systems are operated to perform various bio-processing operations. Such bio-processing operations generally involve processing of genetically engineered organisms, cells, constituents of cells such as proteins, nucleic acids, enzymes, chloroplasts to obtain desired products such as vaccines, hormones, plasma proteins, monoclonal antibodies, or pharmaceuticals, or combinations. The bio-processing operations are classified into upstream operations and downstream operations. To perform the upstream and downstream operations, the bio-processing systems employs various units such as bioreactors, harvesting units, chromatography units, filtration units, buffer preparation units, buffer holding units, media holding units, pumps, temperature management devices, flow control clamps, sensors, and the like.

In traditional bio-processing systems, the units employed to perform the upstream and downstream operations are mechanically and electrically hardwired. By way of example, to perform a given bioprocessing operation, the units in the bio-processing system are mechanically connected to one another via steel pipes. These steel pipes provide a path for transferring fluids between the units. Also, these units in the bio-processing system are powered and controlled via a wired electrical network. Such a configuration of the bio-processing system imposes a critical challenge while modifying the existing configurations of the units in the bio-processing system. Moreover, due to the wired electrical connections in the existing bio-processing systems, monitoring and control of the operations also becomes difficult and space intensive. For example, the sensors cannot be easily positioned at desired locations in the bio-processing system due to routing constraints of the wired connections.

BRIEF DESCRIPTION

In accordance with aspects of the present specification, a bio-processing system is presented. The bio-processing system includes one or more bio-processing units configured to perform at least one bio-processing operation. In addition, the bio-processing system includes one or more process supporting devices operatively coupled to the one or more bio-processing units, where the one or more process supporting devices are configured to aid the one or more bio-processing units in performing the at least one bio-processing operation. Furthermore, the bio-processing system includes one or more sensors operatively coupled to at least one of the one or more bio-processing units and the one or more process supporting devices. Moreover, the bio-processing system also includes a bio-processing workflow controller wirelessly coupled to at least one of the one or more bio-processing units, the one or more process supporting devices, and the one or more sensors, where the bio-processing workflow controller includes a processor configured to create a reconfigurable bio-processing workflow, and where the reconfigurable bio-processing workflow is representative of an arrangement of one or more of the one or more bio-processing units, the one or more process supporting devices, and the one or more sensors to perform the at least one bio-processing operation.

In accordance with another aspect of the present specification, a bio-processing workflow controller for configuring a bio-processing workflow in a bio-processing system is presented. The bio-processing system includes one or more bio-processing units, one or more process supporting devices, and one or more sensors. The bio-processing workflow controller includes a data repository having a catalog of the one or more bio-processing units, the one or more process supporting devices, the one or more sensors, one or more process steps, one or more types of bio-processing workflows, or combinations thereof. In addition, the bio-processing workflow controller includes a processor wirelessly coupled to the bio-processing system. The processor is configured to generate a workflow configuration user interface based on the catalog, where the workflow configuration user interface includes controls configured to aid in customizing an arrangement of one or more of the one or more bio-processing units, the one or more process supporting devices, and the one or more sensors. Further, the processor is configured to receive customization inputs from the workflow configuration user interface to customize the arrangement of one or more of the one or more bio-processing units, the one or more process supporting devices, and the one or more sensors. Moreover, the processor is also configured to create a reconfigurable bio-processing workflow of one or more of the one or more bio-processing units, the one or more process supporting devices, and the one or more sensors based on the customization inputs to perform at least one bio-processing operation.

In accordance with yet another aspect of the present specification, a method for configuring a bio-processing workflow in a bio-processing system is presented. The bio-processing system includes one or more bio-processing units, one or more process supporting devices, one or more sensors, and a bio-processing workflow controller. The method includes generating, by a processor of the bio-processing workflow controller, a workflow configuration user interface based on a catalog of the one or more bio-processing units, the one or more process supporting devices, the one or more sensors, one or more process steps, one or more types of bio-processing workflows, or combinations thereof, where the workflow configuration user interface includes controls configured to aid in customizing an arrangement of one or more of the one or more bio-processing units, the one or more process supporting devices, and the one or more sensors. The method further includes visualizing, by the processor, the workflow configuration user interface on a display unit. Furthermore, the method includes receiving, by the processor, customization inputs from the workflow configuration user interface to customize the arrangement of one or more of the one or more bio-processing units, the one or more process supporting devices, and the one or more sensors. Moreover, the method also includes creating, by the processor, a reconfigurable bio-processing workflow of one or more of the one or more bio-processing units, the one or more process supporting devices, and the one or more sensors based on the customization inputs to perform at least one bio-processing operation.

BRIEF DESCRIPTION OF DRAWINGS

These and other features, aspects, and advantages of the present specification will become better understood when the following detailed description is read with reference to the accompanying drawings in which like characters represent like parts throughout the drawings, wherein.

DETAILED DESCRIPTION

In the following specification and the claims, the singular forms "a", "an" and "the" include plural referents unless the context clearly dictates otherwise. As used herein, the term "or" is not meant to be exclusive and refers to at least one of the referenced components being present and includes instances in which a combination of the referenced components may be present, unless the context clearly dictates otherwise.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable.

In the effort to provide a concise description of these embodiments, all features of an actual implementation may not be described in the specification. It should be appreciated that in the development of any such actual implementation, as in any engineering or design project, numerous implementation-specific decisions must be made to achieve the developer's specific goals such as compliance with system-related and business-related constraints.

As will be described in detail hereinafter, various embodiments of a system and method for configuring a bio-processing workflow in a bio-processing system are presented. The bio-processing system includes one or more bio-processing units, one or more process supporting devices, and one or more sensors. The system and method for configuring a bio-processing workflow aid in creating a reconfigurable bio-processing workflow to allow dynamic modification of the bio-processing workflow. Moreover, the system and method of the present specification also aid in monitoring and controlling of the existing bio-processing workflows.

Figure 1:
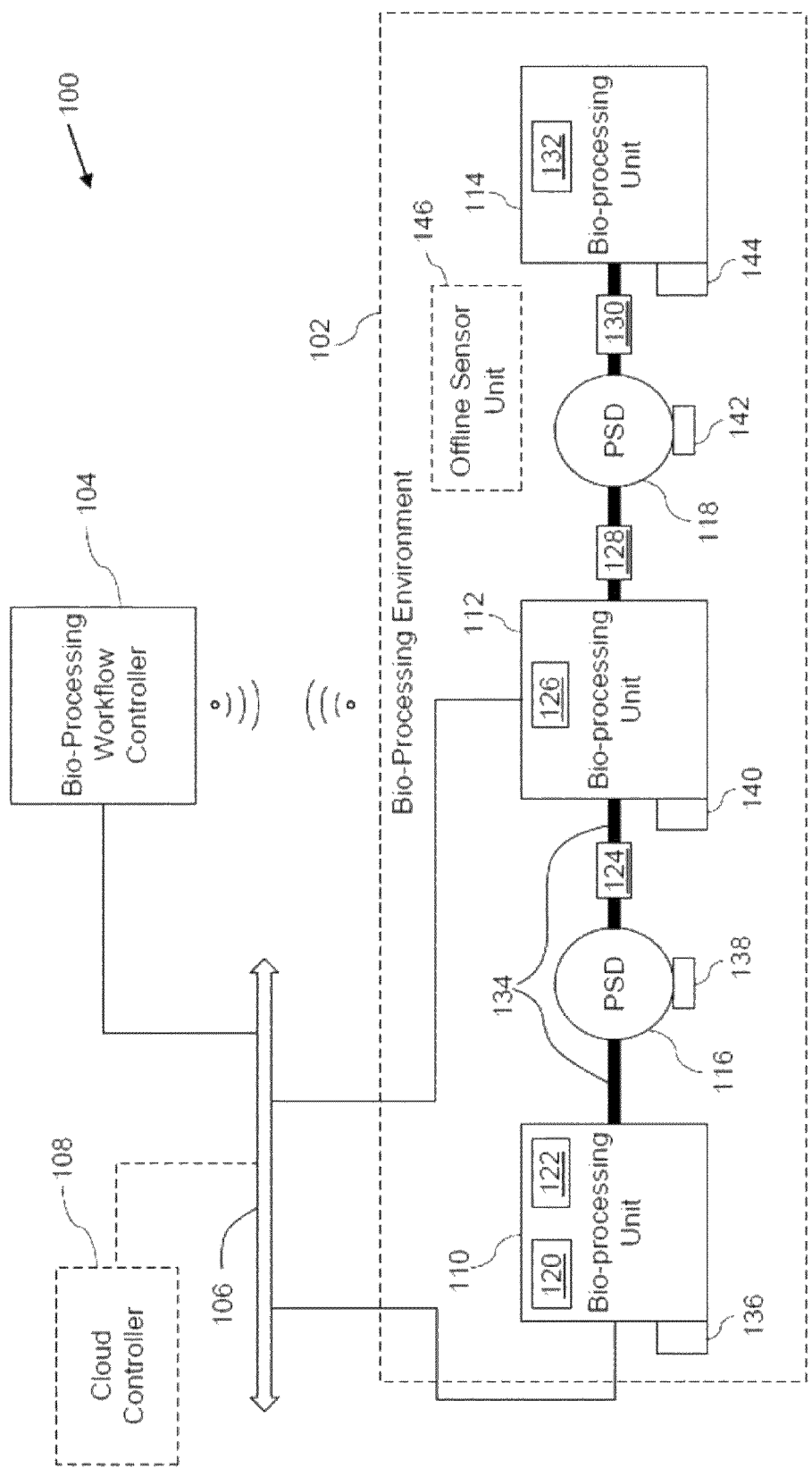
FIG. 1 is a diagrammatic representation of a bio-processing system, in accordance with aspects of the present specification.

FIG. 1 is a diagrammatic representation of a bio-processing system (100), in accordance with aspects of the present specification. The bio-processing system (100) includes a bio-processing environment (102), a bio-processing workflow controller (104), and a communication bus (106). In certain embodiments, the bio-processing system (100) may also include a cloud controller (108). Alternatively, in some embodiments, the bio-processing workflow controller (104) may be implemented on an internet cloud and act as the cloud controller (108). The bio-processing system (100) may be operated to perform various bio-processing operations that may involve processing of genetically engineered organisms, cells, constituents of cells such as proteins, nucleic acids, enzymes, chloroplasts to obtain desired products such as vaccines, hormones, plasma proteins, monoclonal antibodies, or pharmaceuticals, or combinations thereof.

The bio-processing environment (102) may include one or more bio-processing units (110, 112, 114), one or more process supporting devices (116, 118), and one or more sensors (120, 122, 124, 126, 128, 130, 132). The bio-processing units (110, 112, 114) are hereinafter collectively referred to as the bio-processing units (110-114). Also, the sensors (120, 122, 124, 126, 128, 130, 132) are hereinafter collectively referred to as the sensors (120-132). In some embodiments, the bio-processing environment (102) may also include one or more disposable fluid coupling tubes (134) and one or more smart switching devices (136, 138, 140, 142, 144). The smart switching devices (136, 138, 140, 142, 144) are hereinafter collectively referred to as the smart switching devices (136-144). The disposable fluid coupling tubes (134) can suitably be flexible plastic pipes that are used to provide a fluid coupling between one or more of the bio-processing units (110-114), process supporting devices (116, 118), and sensors (120-132). In some embodiments, the disposable fluid coupling tubes (134) may be capable of being bent in any direction to establish a flexible fluid coupling.

In certain embodiments, the bio-processing environment (102) may also include an offline sensor unit (146). The offline sensor unit (146) may be configured to perform one more measurements in the bio-processing environment (102) and/or configured to calibrate the sensors (120-132) in the bio-processing environment (102). In a presently contemplated configuration, the offline sensor unit (146) is within the bio-processing environment (102). However, in other embodiments, the offline sensor unit 146 may be disposed outside the bio-processing environment (102).

The bio-processing units (110-114) may be configured to perform at least one bio-processing operation. Non-limiting examples of the bio-processing units (110-114) may include a bioreactor for cell cultivation, a cell banking unit, a cell harvesting unit, a chromatography unit, a wave rocker, a protein concentration unit, a sterile filtration unit, a virus removal unit, a product holding unit, a buffer preparation unit, a media preparation unit, a buffer holding unit, a media holding unit, or combinations thereof. In the embodiment of FIG. 1, for ease of illustration, the bio-processing environment (102) is shown as including three bio-processing units (110-114). Use of greater than three or lower than three bio-processing units in the bio-processing environment (102) is also envisioned. In some embodiments, the bio-processing units (110-114) may be arranged to perform upstream workflow sub-operations or downstream workflow sub-operations of the bio-processing operation. In some embodiments, while some of the bio-processing units (110-114) may be configured to perform the upstream workflow sub-operations, the remaining processing units of the bio-processing units (110-114) may be configured to perform the downstream workflow sub-operations. Non-limiting examples of the upstream workflow sub-operations may include a cell bank preparation, seed culture expansion, seed production, seed harvesting, or combinations thereof. Also, non-limiting examples of the downstream workflow sub-operations may include chromatography, separation, cell disruption, broth concentration, purification, de-watering, polishing of metabolites, filtration, formulation of a final product, or combinations thereof.

The process supporting devices (116, 118) may be configured to aid the one or more bio-processing units in performing one or more bio-processing operations. Non-limiting examples of the process supporting devices (116, 118) may include a pump, a weighing scale, a flow restriction clamp, a temperature management device, or combinations thereof. The process supporting devices (116, 118) may be operatively coupled to one or more of the bio-processing units (110-114). By way of example, the process supporting device (116) such as a flow restriction clamp may be disposed along the disposable fluid coupling tube (134) between the two bio-processing units (110) and (112) to aid in restricting fluid flow from the bio-processing unit (110) to the bio-processing unit (112). By way of another example, the process supporting device (118) such as a pump may be disposed along a disposable fluid coupling tube (134) between the two bio-processing units (112) and (114) to aid in transferring the fluid from the bio-processing unit (112) to the bio-processing unit (114). A process supporting device such as the temperature management device may be used to maintain a temperature of the fluid within the bio-processing units (110-114) or within the disposable fluid coupling tube (134) at a determined level.

Moreover, the sensors (120-132) are operatively coupled to at least one of the bio-processing units (110-114) and the process supporting devices (116, 118) and configured to monitor one or more process parameters. The sensors (120-132) may be disposed within the bio-processing units (110-114) and/or disposed along the disposable fluid coupling tubes (134) between the bio-processing units (110-114). For example, some sensors, such as the sensors (120, 122, 126, and 132) are disposed within the bio-processing units (110-114). Sensors (124, 128, and 130) are disposed along the disposable fluid coupling tubes (134) between the bio-processing units (110-114). Non-limiting examples of the sensors (120-132) may include a pressure sensor, a temperature sensor, a pH sensor, a conductivity sensor, a glucose sensor, a biomass sensor, a cell viability sensor, an oxygen sensor, a carbon-dioxide sensor, an ultraviolet (UV) sensor, a flow sensor, a foam sensor, or combinations thereof.

The process parameters monitored by these sensors (120-132) may include a pressure of the fluid in the disposable fluid coupling tubes (134), a pressure differential of the fluid in the disposable fluid coupling tubes (134), a temperature of the fluid, a pH of the fluid, a presence of a biomass in the fluid, an electrical conductivity of the fluid, a level of glucose in the fluid, a cell viability in the fluid, a level of oxygen in the bio-processing units (110-114), a level of carbon-dioxide in the bio-processing units (110-114), a flow rate of the fluid, a level of foam in the fluid in the bio-processing units (110-114), or combinations thereof.

In some embodiments, one or more of the bio-processing units (110-114), the process supporting devices (116, 118), and the sensors (120-132) may include a wireless communication unit (not shown). The wireless communication unit may be configured to establish a wireless connection between one or more of the bio-processing units (110-114), the process supporting devices (116, 118), and the sensors (120-132) and the bio-processing workflow controller (104). In certain embodiments, the wireless communication unit may be implemented using hardware and/or software. The wireless communication unit may also include circuits capable of communicating with the bio-processing workflow controller (104) via wireless communication techniques such as, but not limited to, infrared, short-range radio frequency (RF) communication, Bluetooth, Bluetooth low energy (BLE), Wi-Fi, Wi-Max, mobile communication techniques such as Global System for Mobile communication (GSM), General Packet Radio Service (GPRS), Code Division Multiple Access (CDMA), High-Speed Downlink Packet Access (HSDPA), 2.5G, 3G, 4G, 5G, or combinations thereof.

As previously noted, the offline sensor unit (146) may be configured to perform one more measurements in the bio-processing environment (102) and/or calibrate the sensors (120-132) in the bio-processing environment (102). More particularly, in certain embodiments, the offline sensor unit (146) may include a cell analyzer having one or more sensors (not shown) to selectively determine one or more the process parameters. The sensors in the cell analyzer of the offline sensor unit (146) may be similar to the sensors (120-132). Accordingly, the sensors in the cell analyzer may also be configured to measure the process parameters such as pH, conductivity, viable cell density, total cell density, nutrients such as glucose and glutamine, metabolites such as lactate, glutamate, ammonia, and combinations thereof. In certain embodiments, a fluid may be extracted, manually or using robotics, from one or more of the bio-processing units (110-114). The extracted fluid may be analyzed using the cell analyzer of the offline sensor unit (146) to measure the process parameters. In some embodiments, the offline sensor unit (146) may also be configured to calibrate one or more of the sensors (120-132). In certain embodiments, the calibration of the sensors (120-132) may include determining accuracy of measurements performed by the sensors (120-132) with reference to similar measurements performed by the sensors of the offline sensor unit (146).

Moreover, the offline sensor unit (146) may also include a wireless communication unit similar to the wireless communication units of the bio-processing units (110-114), the process supporting devices (116, 118), and the sensors (120-132). In certain embodiments, the offline sensor unit (146) may be configured to communicate data regarding the measured process parameters to the bio-processing workflow controller (104) via the wireless communication unit.

In certain embodiments, the wireless communication units of the bio-processing units (110-114), the process supporting devices (116, 118), the sensors (120-132), and the offline sensor unit (146) may be configured to download or update a firmware in the respective bio-processing units (110-114), process supporting devices (116, 118), sensors (120-132), and offline sensor unit (146) to update or enhance their corresponding operations. The wireless communication units may be configured to download/update the firmware from the cloud controller (108), in some embodiments.

In certain embodiments, the bio-processing environment (102) may also include the one or more smart switching devices (136-144). In the embodiment of FIG. 1, one smart switching device is shown as being electrically coupled to each of the bio-processing units (110-114) and each of the process supporting devices (116, 118). This arrangement allows supply of electric power to the bio-processing units (110-114) and the process supporting devices (116, 118) via a corresponding smart switching device. In particular, the bio-processing units (110-114) and the process supporting devices (116, 118) are coupled to respective electric power ports (not shown) via corresponding smart switching devices (136-144). In FIG. 1, the bio-processing units (110, 112, and 114) are coupled to their respective electric power ports via the smart switching devices (136, 140, and 144), respectively. Similarly, the process supporting devices (116, 118) are coupled to their respective electric power ports via the smart switching devices (138 and 142), respectively.

The smart switching devices (136-144) may include an input port, an output port, a wireless communication interface, and a switch controlled via a wireless communication unit. The wireless communication unit of the smart switching device may be representative of one embodiment of the wireless communication unit of the bio-processing units (110-114), the process supporting devices (116, 118), and the sensors (120-132). The input port of the smart switching device is coupled to an electric power port to receive electric power. The output port of the smart switching device is coupled to a corresponding bio-processing unit (110-114) or process supporting device (116, 118) to supply the electric power. Further, the switch may be controlled to enable or disable an electrical connection between the input port and the output port of the smart switching device based on an operating state of the switch.

In some embodiments, the smart switching device (136-144) is configured to enable or disable supply of power to the corresponding one of the bio-processing units (110-114) and the process supporting devices (116, 118) based on a current signature of electric current drawn by the respective one of the bio-processing units (110-114) and the process supporting devices (116, 118). The current signature is representative of one or more properties of the electric current. By way of example, the current signature may include information about a magnitude, frequency, phase, harmonics, or combinations thereof, of the electric current. In certain instances, any abnormality in the current signature may be indicative of a fault or malfunctioning of the corresponding one of the bio-processing units (110-114) and the process supporting devices (116, 118). Therefore, in some embodiments, the wireless communication unit of the smart switching device is configured to analyze the current signature of the electric current drawn by the corresponding bio-processing unit (110-114) or the process supporting device (116, 118). Accordingly, if an abnormal current signature is identified, the wireless communication unit of the smart switching device is configured to deactivate the switch to disable the supply of power to that unit or device.

In certain embodiments, a processor in the bio-processing workflow controller (104) is configured to control the operation of the smart switching devices (136-144) based on the process parameters. The smart switching device (136-144) will be described in greater detail in conjunction with the flow diagram of FIG. 5.

The bio-processing workflow controller (104) is wirelessly coupled to at least one of the bio-processing units (110-114), the process supporting devices (116, 118), and the sensors (120-132). In some embodiments, the bio-processing workflow controller (104) may be coupled to one or more of the bio-processing units (110-114) via a communication bus (106). The communication bus (106) may be a field bus such as Profibus®, Modbus®, Controller Area Network (CAN) bus, FOUNDATION Fieldbus® or an industrial Ethernet bus such Transmission Control Protocol/Internet Protocol (TCP/IP) bus, Modbus® TCP bus, Profinet® Ethernet bus, EtherCAT® Ethernet bus, or combinations thereof.

In the embodiment of FIG. 1, the bio-processing workflow controller (104) is shown as being disposed outside the bio-processing environment (102). In certain embodiments, the bio-processing workflow controller (104) may be disposed locally within the bio-processing environment (102). In certain other embodiments, the bio-processing workflow controller (104) may be disposed at a location remote from the bio-processing environment (102).

In some embodiments, the bio-processing workflow controller (104) may be configured to create a reconfigurable bio-processing workflow. The reconfigurable bio-processing workflow is representative of an arrangement of one or more of the bio-processing units (110-114), the process supporting devices (116, 118), the sensors (120-132), the disposable fluid coupling tubes (134), and the smart switching devices (136-144) to perform the desired bio-processing operation. One example of a bio-processing workflow in the bio-processing environment (102) is depicted in FIG. 1. In particular, the bio-processing workflow of FIG. 1 includes the bio-processing environment (102) having a determined sequence/arrangement of the bio-processing units (110-114), the process supporting devices (116, 118), the sensors (120-132), the disposable fluid coupling tubes (134), and the smart switching devices (136-144) to perform the bio-processing operation. By way of example, an order of the determined sequence includes the bio-processing unit (110) with the sensors (120, 122), the process supporting device (116), the sensor (124), the bio-processing unit (112) with the sensor (126), the sensor (128), the process supporting device (118), the sensor (130), and the bio-processing unit (114) with the sensor (132).

Moreover, in accordance with aspects of the present specification, the bio-processing workflow controller (104) is configured to dynamically reconfigure the bio-processing workflow. In some embodiments, the bio-processing workflow controller (104) is also configured to generate and visualize a workflow configuration user interface (see FIG. 3) to a user or operator of the bio-processing system (100). The workflow configuration user interface facilitates creation and/or reconfiguration of the bio-processing workflow. In certain embodiments, the bio-processing workflow controller (104) may also be configured to monitor and control the bio-processing workflow. The bio-processing workflow controller (104) will be described in greater detail in conjunction with FIGS. 2-5.

Figure 2:
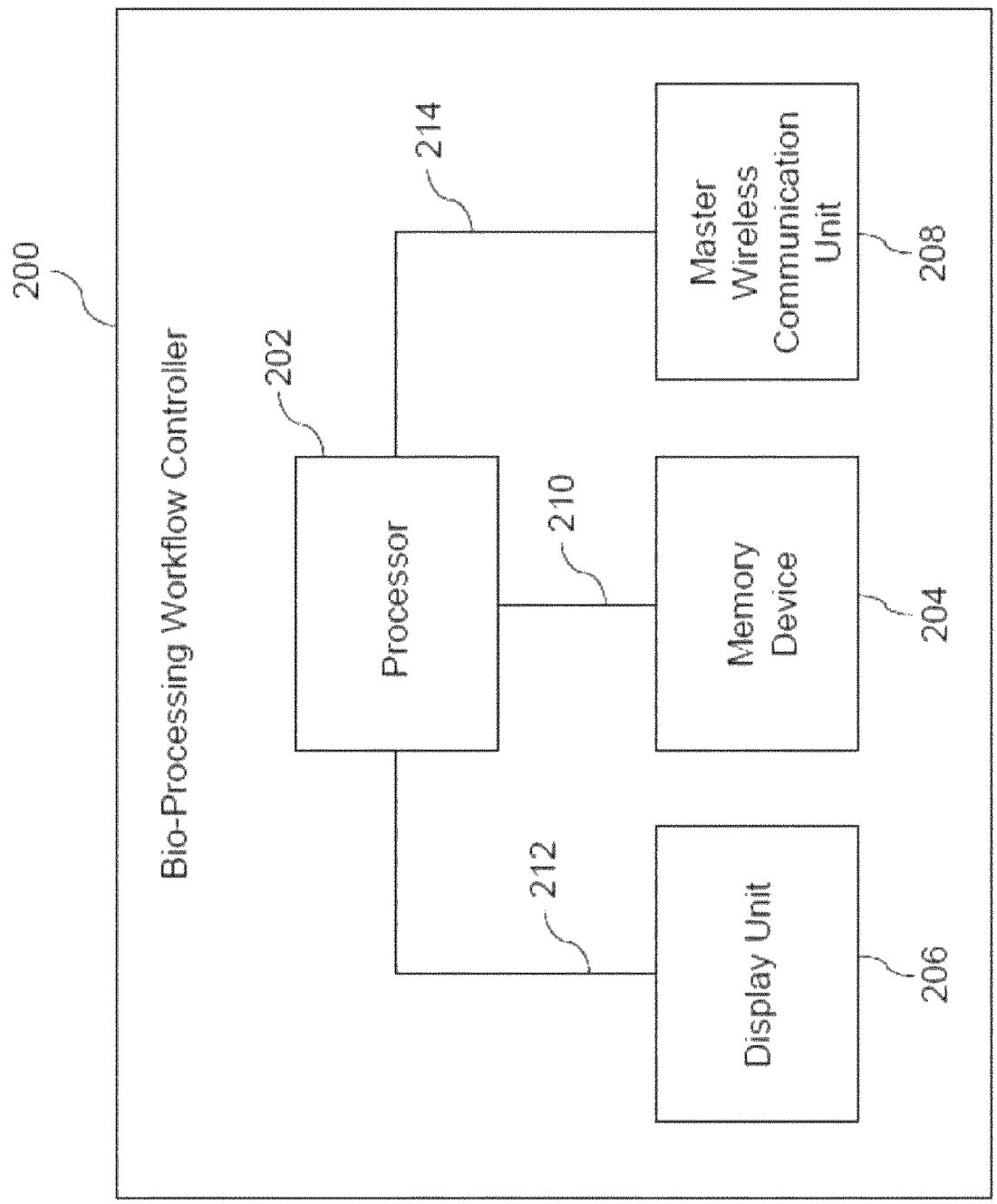
FIG. 2 is a diagrammatic representation of a bio-processing workflow controller for use in the bio-processing system of FIG. 1, in accordance with aspects of the present specification.

Referring now to FIG. 2, a diagrammatic representation of a bio-processing workflow controller (200), in accordance with aspects of the present specification, is presented. The bio-processing workflow controller (200) is representative of one embodiment of the bio-processing workflow controller (104) of FIG. 1. FIG. 2 is described in conjunction with the components of FIG. 1.

The bio-processing workflow controller (200) includes a processor (202), a memory device (204), a display unit (206), and a master wireless communication unit (208). The processor (202) may be coupled to the memory device (204), the display unit (206), and the master wireless communication unit (208) and configured to control operations of the memory device (204), the display unit (206), and the master wireless communication unit (208). In one embodiment, the processor (202) is coupled to the memory device (204), the display unit (206), and the master wireless communication unit (208) via data and control lines (210), (212), and (214), respectively.

The processor (202) may include hardware such as electronic circuits, software, and/or firmware for performing various arithmetic, logical, and/or graphics processing operations. The processor (202) may be in the form of an integrated circuit (IC) chip. The processor (202) may have one or more processing cores to aid in the arithmetic, logical, and/or graphics processing operations. The memory device (204) may be configured to store data and program instructions that are accessible by the processor via the data and control line (210). Also, the memory device (204) may include random access memory (RAM) such as a static RAM (SRAM) and a dynamic RAM (DRAM), a read-only memory (ROM) such as a masked ROM (MROM), a programmable ROM (PROM), an erasable and programmable ROM (EPROM), and an electrically erasable and programmable ROM (EEPROM). Moreover, the memory device (204) may be in the form of a compact disc (CD), a digital versatile disc (DVD), a floppy disc, a USB flash drive, a cloud based memory, or combinations thereof.

In some embodiments, the memory device (204) may be configured to store a data repository. The data repository may include a catalog and/or a look-up table of the bio-processing units (110-114), the process supporting devices (116, 118), the sensors (120-132), the smart switching devices (136-144), workflow types, workflow sub-processes, or combinations thereof. In particular, the catalog and/or the look-up table may include identity information, such as a unique ID, corresponding to the bio-processing units (110-114), the process supporting devices (116, 118), the sensors (120-132), the smart switching devices (136-144), one or more process steps, one or more types of bio-processing workflows, or combinations thereof. The unique ID may include a name, a numerical value, a special character, a symbol, or combinations thereof.

In some embodiments, the catalog and/or the look-up table may be updated to include identity information corresponding to a new bio-processing unit, process supporting device, sensor, process step, disposable fluid coupling tube that may be introduced in the bio-processing environment (102). Additionally, in certain embodiments, the stored identity information may be updated when any of the existing bio-processing unit, process supporting device, sensor, process step, disposable fluid coupling tube is replaced or modified in the bio-processing environment (102). When the identity information is stored or updated, the processor (202) may be configured to update the catalog and/or look-up table to include the newly added or updated identity information.

The display unit (206) may be implemented using a cathode ray tube (CRT) display, a liquid crystal display (LCD), a light-emitting diode (LED) display, a plasma display, a projector, or combinations thereof. In some embodiments, the display unit (206) may be a touchscreen based display. The display unit (206) may be configured to receive commands and data from the processor (202) and update information displayed thereon based on the received command and data. More particularly, a user interface such as a workflow configuration user interface (see FIG. 3) may be visualized on the display unit (206). In some embodiments, the workflow configuration user interface facilitates creation of a reconfigurable workflow by the processor (202).

The master wireless communication unit (208) may be implemented using hardware and/or software. The master wireless communication unit (208) includes circuits capable of wirelessly communicating with the wireless communication units of the bio-processing units (110-114), the process supporting devices (116, 118), and the sensors (120-132), and the smart switching devices (136-144). The master wireless communication unit (208) is wirelessly coupled to the wireless communication unit corresponding to the bio-processing units (110-114), the process supporting devices (116, 118), the sensors (120-132), and the smart switching devices (136-144). Moreover, the master wireless communication unit (208) is configured to communicate at least one of control commands and data between the processor (202) and the wireless communication units of the bio-processing units (110-114), the process supporting devices (116, 118), the sensors (120-132), and the smart switching devices (136-144). The wireless communication facilitated by the master wireless communication unit (208) may be enabled via wireless communication techniques such as, but not limited to, infrared, short-range radio frequency (RF) communication, Bluetooth, Bluetooth low energy (BLE), Wi-Fi, Wi-Max, mobile communication techniques such as Global System for Mobile communication (GSM), General Packet Radio Service (GPRS), Code Division Multiple Access (CDMA), High-Speed Downlink Packet Access (HSDPA), 2.5G, 3G, 4G, 5G, or combinations thereof.

In certain embodiments, the processor (202) may be configured to download/update the program instructions, the catalog/look-up table, and/or the firmware via the master wireless communication unit (208). The processor (202) may be configured to download/update the program instructions, the catalog/look-up table, and/or the firmware from the cloud controller (108), in some embodiments.

During operation of the bio-processing system (100), the processor (202) is configured to facilitate creation of a reconfigurable bio-processing workflow that is representative of an arrangement of one or more of the bio-processing units (110-114), the process supporting devices (116, 118), the sensors (120-132), the disposable fluid coupling tubes (134), and the smart switching devices (136-144) to perform a bio-processing operation. In some embodiments, the processor (202) may also be configured to monitor and control the reconfigurable bio processing workflow. The bioprocessing workflow controller 200 will be described in greater detail in conjunction with FIGS. 3-5.

Figure 3:
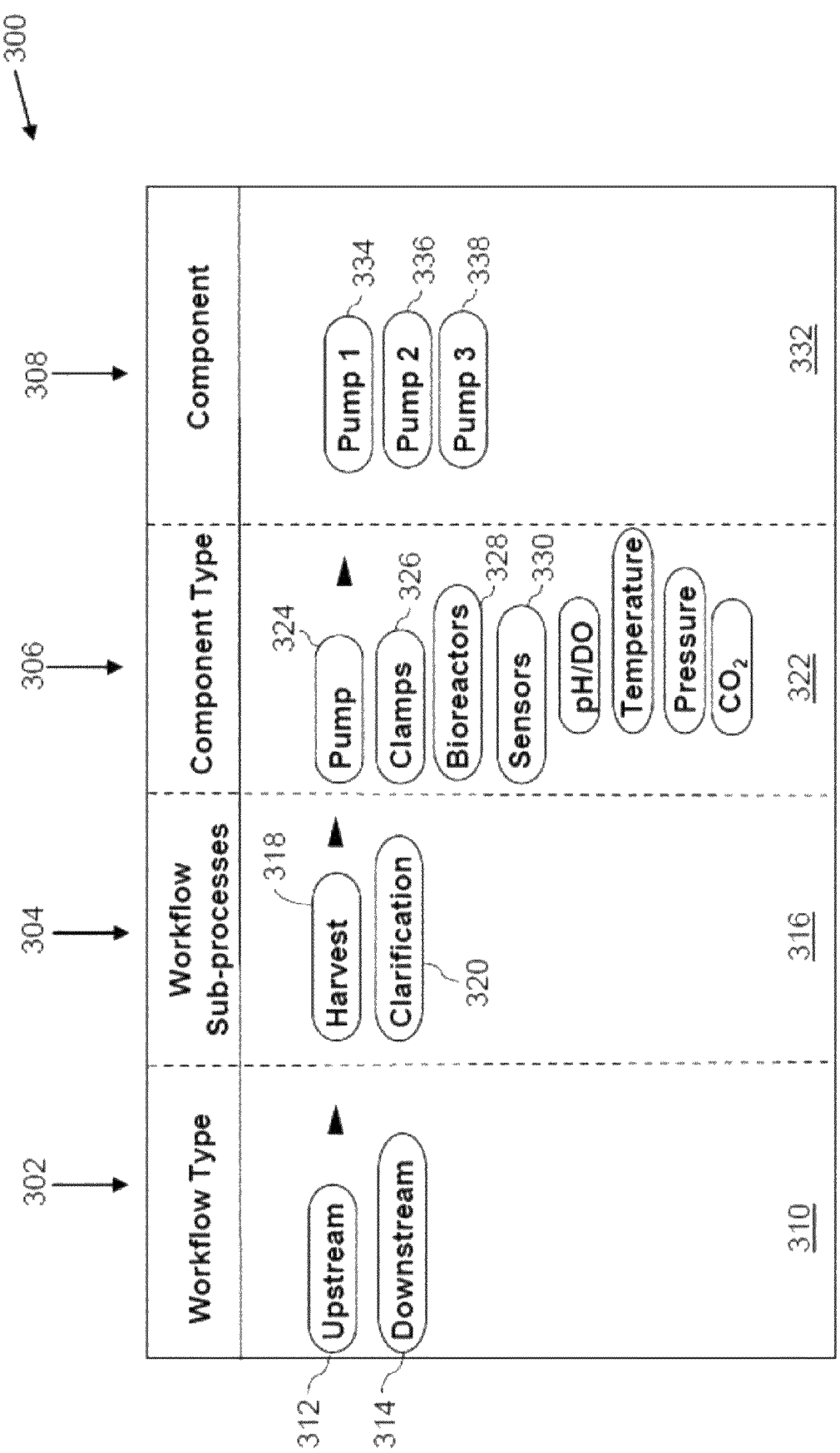
FIG. 3 is a snapshot of an example workflow configuration user interface, in accordance with aspects of the present specification.

FIG. 3 is a snapshot of an example workflow configuration user interface (300), in accordance with aspects of the present specification. FIG. 3 is described in conjunction with the bio-processing workflow controller (200) of FIG. 2. The workflow configuration user interface (300) may be generated by the processor (202) of the bio-processing workflow controller (200) using the catalog/look-up table stored in the data repository of the memory device (204). Moreover, the processor (202) is configured to visualize the workflow configuration user interface (300) on the display unit (206).

The workflow configuration user interface (300) includes one or more columns, representing workflow types (302), workflow sub-processes (304), component types (306), and components (308). Although the workflow types (302), the workflow sub-processes (304), the component types (306), and the components (308) are shown as columns in the workflow configuration user interface (300), use of other types of objects such as dropdown lists, radial buttons, individual icons, or combinations thereof, is also contemplated.

In some embodiments, the workflow configuration user interface (300) allows a user to reconfigure or create a bio-processing workflow. In particular, the user may select a workflow type (302) in the workflow configuration user interface (300). Consequent to the user selection, a sub-menu (310) is visualized in the workflow configuration user interface (300). In certain embodiments, the sub-menu (310) may be visualized in the workflow configuration user interface (300) by default. The sub-menu (310) includes one or more options for the workflow type, for example, an upstream workflow option (312) and a downstream workflow option (314). Based on a selection by the user of any of the upstream workflow option (312) and the downstream workflow option (314), a corresponding sub-menu (316) is visualized in the workflow configuration user interface (300). For example, the sub-menu (316) corresponds to the upstream workflow option (312) and includes workflow sub-processes corresponding to the upstream workflow. The workflow sub-processes options of the upstream workflow may include operations such as harvest (318) and clarification (320).

Subsequent to a selection of one of the harvest (318) or the clarification (320) operations, a corresponding sub-menu (322) is visualized in the workflow configuration user interface (300). For example, the sub-menu (322) corresponds to the harvest operation (318) and includes component types that may be employed in the harvest operation (318) of the upstream workflow. By way of example, the sub-menu (322) includes various options of the components types such as a pump option (324), a clamp option (326), a bio-reactor option (328), a sensor option (330), or combinations thereof, that may be used in the harvest operation of the upstream workflow.

Once a selection of the component type is initiated, a corresponding sub-menu (332) is visualized in the workflow configuration user interface (300). For example, the sub-menu (332) corresponds to components that may be used for the harvest operation (318). By way of example, the sub-menu (332) includes various options of the components such as "pump 1" (334), "pump 2" (336), and "pump 3" (338). Any of the options (334, 336, 338) may be selected to include a corresponding pump in the workflow.

Although not shown in FIG. 3, the workflow configuration user interface (300) may also include one or more menu options to visualize a configured or customized workflow. In one example, the customized workflow may be visualized in the form of a block diagram representation that includes various components that are selected to implement/generate the customized workflow. More particularly, the block diagram representation of the customized workflow may include a block for each selected component and the corresponding interconnections with other components in the customized workflow. Accordingly, a visual representation of the configured or customized workflow to perform a desired bio-processing operation may be visualized on the workflow configuration user interface (300).

Implementing the workflow configuration user interface (300) as described hereinabove allows the user to create a customized bio-processing workflow. Additionally, a currently existing bio-processing workflow may be reconfigured using the workflow configuration user interface (300).

Figure 4:
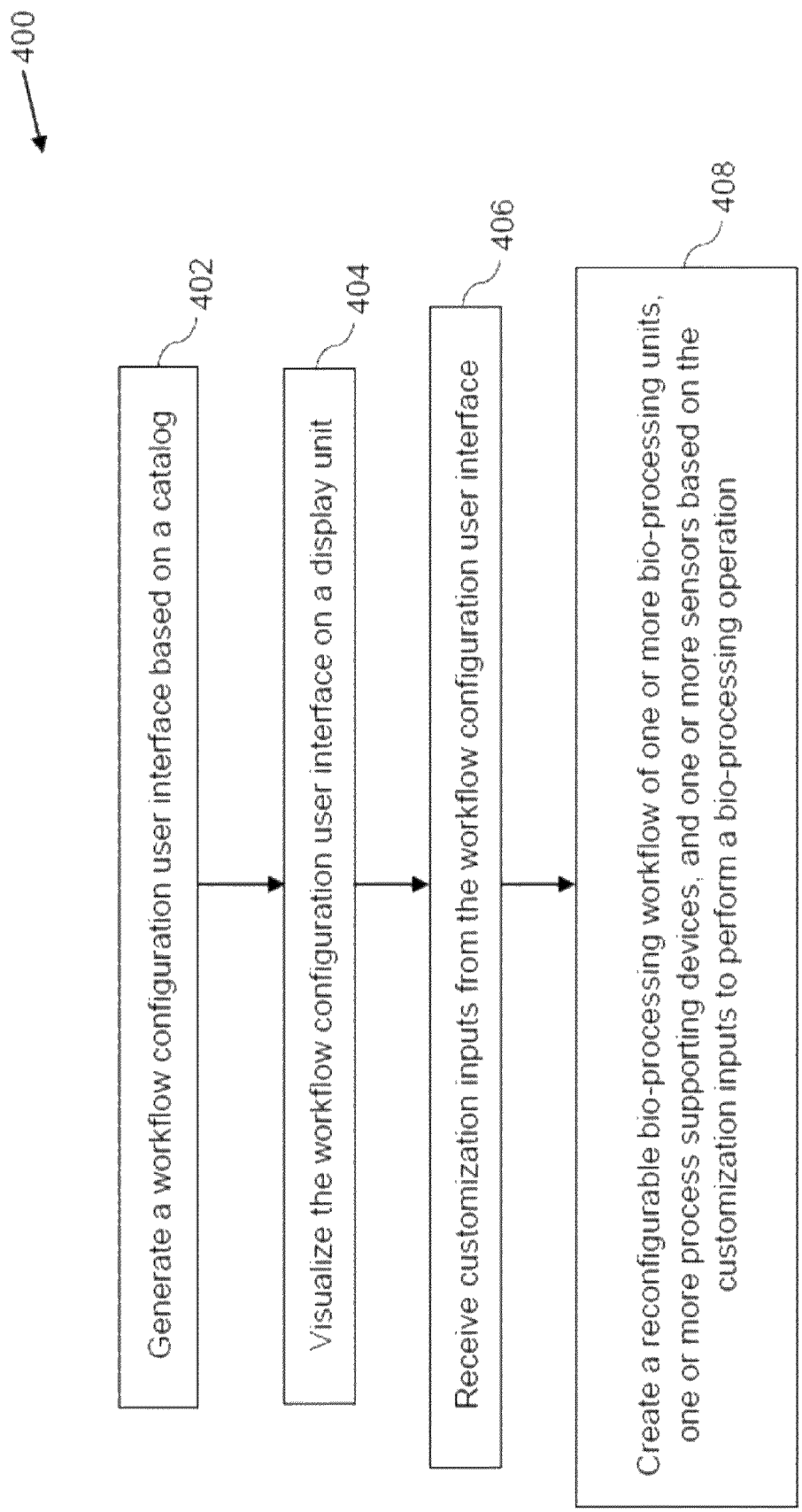
FIG. 4 is a flow diagram of an example method for configuring a bio-processing workflow, in accordance with aspects of the present specification.

FIG. 4 is a flow diagram (400) of an example method for configuring a bio-processing workflow, in accordance with aspects of the present specification. FIG. 4 is described in conjunction with the components of FIGS. 1-3.

At step (402), the processor (202) is configured to generate a workflow configuration user interface such as the workflow configuration user interface (300) based on the catalog and/or look-up table. As previously described, the catalog includes identity information, such as a unique ID corresponding to the bio-processing units (110-114), the process supporting devices (116, 118), the sensors (120-132), the smart switching devices (136-144), one or more process steps, one or more types of bio-processing workflows, or combinations thereof.

In some embodiments, to generate the workflow configuration user interface (300), the processor (202) may be configured to arrange the information acquired from the catalog/look-up table in a predefined user interface template. It may also be noted that if the catalog has been updated, the processor (202) is further configured to update the arrangement of the information in the predefined user interface template to generate the workflow configuration user interface (300). In some embodiments, the workflow configuration user interface (300) generated at the step (402) may include controls such as menu options (302-338) configured to aid in customizing the arrangement of one or more of the bio-processing units (110-114), the process supporting devices (116, 118), the sensors (120-132), the disposable fluid coupling tubes (134), and the smart switching devices (136-144) to create the bio-processing workflow.

Further, at step (404), the processor (202) is configured to visualize the workflow configuration user interface (300) on the display unit (206). More particularly, the processor (202) may be configured to communicate data representative of the workflow configuration user interface (300) to the display unit (206) to aid in visualizing the workflow configuration user interface (300) on the display unit (206).

Also, the processor (202) may be configured to receive customization inputs from the workflow configuration user interface (300), as indicated by step (406). In some embodiments, if the display unit (206) includes a touchscreen input capability, the processor (202) may be configured to receive the customization inputs via the display unit (206). In other embodiments, the processor (202) may be configured to receive the customization inputs via one or more input devices (not shown) that are operatively coupled to the bio-processing workflow controller (200).

The customization inputs may include an input indicative of the selection of one or more of the workflow type, workflow sub-processes, component type, and components via the workflow configuration user interface (300). In some embodiments, the customization inputs may also include selections for routing and positioning of the components. By way of example, the customization inputs may include selection of a workflow type such as upstream workflow option (312), an upstream operation such as harvest (318), a component type such as the pump (324), and a component such as the "Pump 1" (334), as depicted in FIG. 3. These customization inputs indicative of the upstream sub-operation are received by the processor (202). Other customization inputs may be received in a similar fashion. In certain embodiments, the customization inputs are also indicative of modifications to be made to an existing bio-processing workflow. For example, the customization inputs may be indicative of addition, removal, re-ordering, substitution, or replacing of any of the components in the reconfigurable bio-processing workflow.

Moreover, at step (408), the processor (202) is configured to create a reconfigurable bio-processing workflow based on the customization inputs received at step (406) to perform a bio-processing operation. The reconfigurable bio-processing workflow is representative of a logical arrangement of the bio-processing units (110-114), the process supporting devices (116, 118), the sensors (120-132), the disposable fluid coupling tubes (134), and the smart switching devices (136-144) to perform the bio-processing operation.

In some embodiments, once the reconfigurable bio-processing workflow is created by the processor (202), a physical workflow in the bio-processing environment (102) of FIG. 1 may be configured manually by arranging and interconnecting components in accordance with the reconfigurable bio-processing workflow created at step (408) to perform the corresponding bio-processing operation. In one embodiment, the arrangement of the components in the bio-processing environment (102) of FIG. 1 may be representative of the physical bio-processing workflow that is configured based on the reconfigurable bio-processing workflow created at the step (408).

Figure 5:
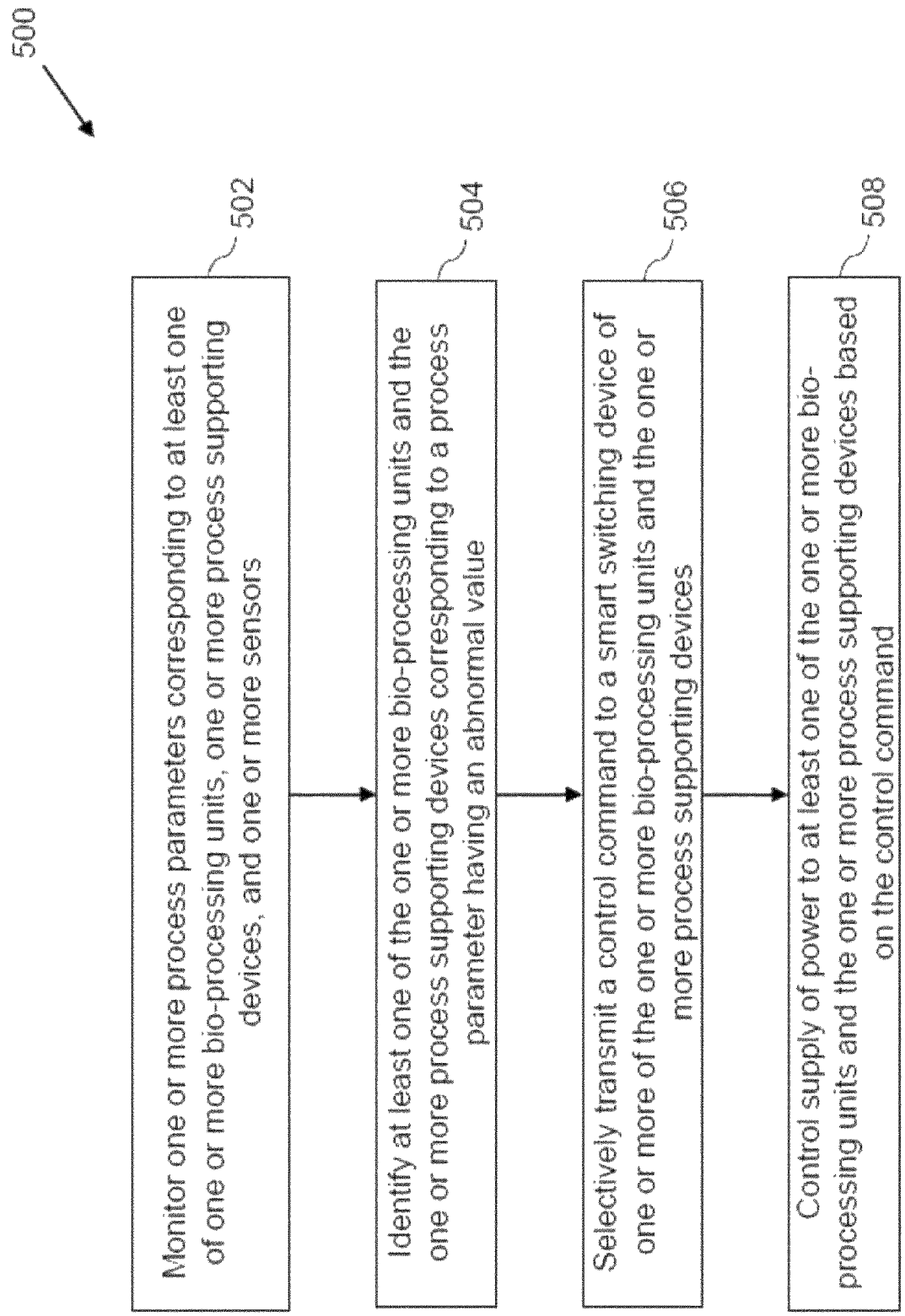
FIG. 5 is a flow diagram of an example method for monitoring and controlling a bio-processing workflow, in accordance with aspects of the present specification.

Moreover, in certain embodiments, the method of configuring the bio-processing workflow of FIG. 4 may additionally include steps for monitoring and controlling the existing reconfigurable bioprocessing workflow. Turning now to FIG. 5, a flow diagram (500) of an example method for monitoring and controlling the reconfigurable bio-processing workflow, in accordance with aspects of the present specification, is presented. The method (500) of FIG. 5 is described with reference to the components of FIGS. 1-4.

At step (502), the processor (202) is configured to monitor one or more process parameters corresponding to at least one of one or more bio-processing units (110-114), the one or more process supporting devices (116, 118), and one or more sensors (120-132). Some examples of the process parameters that may be monitored by the processor (202) may include, but are not limited to, the pressure of the fluid in the disposable fluid coupling tubes (134), the pressure differential of the fluid in the disposable fluid coupling tubes (134), the temperature of the fluid, the pH of the fluid, the presence of a biomass in the fluid, the electrical conductivity of the fluid, the level of glucose in the fluid, the cell viability in the fluid, the level of oxygen in the bio-processing units (110-114), the level of carbon-dioxide in the bio-processing units (110-114), the flow rate of the fluid, the level of foam in the fluid in the bio-processing units (110-114), or combinations thereof. The processor (202) may receive values of the process parameters from the sensors (120-132).

In some embodiments, the monitoring may also include comparing the values of the process parameters with corresponding threshold values or corresponding predetermined ranges to identify any abnormality in the values of the process parameters. Based on the comparison, if the values of the process parameters are identified to be normal, the processor (202) may determine that components in the bio-processing workflow are operating normally. However, if the values of one or more of the process parameters are identified to be abnormal, the processor (202) is configured to identify at least one of the bio-processing units (110-114) and the process supporting devices (116, 118) that corresponds to the process parameter having an abnormal value as an abnormal device or malfunctioning device, as indicated by step 504. By way of example, if an abnormality in a value of a pressure of the fluid subsequent to the process supporting device (118) is detected, the processor (202) may identify the process supporting device (118) as an abnormal device.

In order to protect the bio-processing environment (102) from any hazards that may arise from such abnormalities, it is desirable to control propagation of such abnormalities. To that end, in some embodiments, at step 506, the processor (202) is configured to selectively transmit a control command to the smart switching device corresponding to one or more of the bio-processing units (110-114) and the process supporting devices (116, 118) that have been identified as an abnormal device at step 504. More particularly, the processor (202) is configured to transmit the control command to the smart switching device connected to the abnormal or malfunctioning bio-processing unit (110-114) and/or process supporting device (116, 118) having the abnormality. The control command may be indicative of an instruction to discontinue supply of electric power to the identified bio-processing unit (110-114) and/or the process supporting device (116, 118). By way of example, at step 504, if the process supporting device (118) is identified as having abnormal values of the process parameter, the processor (202) is configured to wirelessly transmit the control command to the smart switching device (142) of the process supporting device (118).

Moreover, at step (508), supply of power to the identified abnormal/malfunctioning bio-processing units (110-114) and/or the process supporting devices (116, 118) may be controlled based on the control command. In some embodiments, the control command may be received by the smart switching device of the identified abnormal bio-processing units (110-114) and/or the process supporting devices (116, 118). In particular, the control command may be received by a wireless communication unit of the smart switching device. The wireless communication unit in turn sends a control signal to the switch within the smart switching device. The switch within the smart switching device is in turn operated in a non-conducting state to discontinue supply of the power to the bio-processing unit or the process supporting device connected to the smart switching device. Accordingly, functioning of the identified abnormal bio-processing units (110-114) and/or the process supporting devices (116, 118) may be stopped. In certain embodiments, the processor (202) may also be configured to generate and communicate an alert to the operator of the bio-processing system (100) to indicate a requirement to clear the fault.

Any of the foregoing steps may be suitably replaced, reordered, or removed, and additional steps may be inserted, depending on the needs of a particular application.

Various embodiments of a bio-processing system having an exemplary bio-processing workflow controller and a method for configuring a bio-processing workflow are presented. The bio-processing workflow controller facilitates creations of reconfigurable bio-processing workflows in the bio-processing system. Moreover, the bio-processing workflow controller also facilitates modification/reconfiguration of an existing bio-processing workflow. The creation and/or modification of the bio-processing workflows is enabled at least in part by generating and visualizing a workflow configuration user interface on a display and receiving customization inputs. Accordingly, the bio-processing system—and method enhance the flexibility and reusability of the bio-processing units, process supporting devices, sensors, and smart switching devices in the bio-processing environment. Furthermore, the bio-processing workflow controller is wirelessly connected to the bio-processing units, process supporting devices, sensors, and smart switching devices in the bio-processing environment. Accordingly, process parameters of the bio-processing environment are monitored wirelessly. Use of the bio-processing units, process supporting devices, sensors, and smart switching devices with wireless communication capability greatly enhances scalability of the bio-processing environment. Moreover, use of the smart switching devices aids in intelligently controlling the bio-processing workflows.

It will be appreciated that variants of the above disclosed and other features and functions, or alternatives thereof, may be combined to create many other different applications. Various unanticipated alternatives, modifications, variations, or improvements therein may be subsequently made by those skilled in the art and are also intended to be encompassed by the following claims.

The invention claimed is:

1. A bio-processing system, comprising:
one or more bio-processing units comprising a bioreactor for cell cultivation, configured to perform at least one bio-processing operation;
one or more process supporting devices, selected from a pump, a weighing scale, a flow restriction clamp, a temperature management device, or a combination thereof, operatively coupled to the one or more bio-processing units, wherein the one or more process supporting devices are configured to aid the one or more bio-processing units in performing the at least one bio-processing operation;
one or more sensors operatively coupled to at least one of the one or more bio-processing units and the one or more process supporting devices;
a bio-processing workflow controller wirelessly coupled to at least one of the one or more bio-processing units, the one or more process supporting devices, and the one or more sensors, wherein the bio-processing workflow controller comprises:
  a processor configured to create a reconfigurable bio-processing workflow, and wherein the reconfigurable bio-processing workflow is representative of an arrangement of one or more of the one or more bio-processing units, the one or more process supporting devices, and the one or more sensors to perform the at least one bio-processing operation; and
  a data repository comprising a listing of the one or more bio-processing units, the one or more process supporting devices, the one or more sensors, one or more process steps, one or more types of bio-processing workflows, or combinations thereof; and
one or more flexible fluid coupling tubes configured to facilitate fluid communication between the one or more bio-processing units, the one or more process supporting devices, and the one or more sensors.

2. The bio-processing system of claim 1, wherein the one or more bio-processing units further comprise a wave rocker, a cell banking unit, a cell harvesting unit, a chromatography unit, a protein concentration unit, a sterile filtration unit, a virus removal unit, a product holding unit, a buffer preparation unit, a media preparation unit, a buffer holding unit, a media holding unit, or combinations thereof, wherein the one or more process supporting devices comprise a pump, a weighing scale, a flow restriction clamp, a temperature management device, or combinations thereof, and wherein the one or more sensors comprise a pressure sensor, a temperature sensor, a pH sensor, a conductivity sensor, a glucose sensor, a biomass sensor, a cell viability sensor, an oxygen sensor, a carbon-dioxide sensor, an ultraviolet sensor, a flow sensor, a foam sensor, or combinations thereof.

3. The bio-processing system of claim 1, wherein at least one of the one or more sensors is disposed along one or more of the disposable fluid coupling tubes.

4. The bio-processing system of claim 1, wherein the one or more sensors are disposed within at least one of the one or more bio-processing units and the one or more process supporting devices.

5. The bio-processing system of claim 1, wherein the bio-processing controller comprises a master wireless communication unit configured to communicate at least one of control commands and data between the bio-processing workflow controller and the one or more bio-processing units, the one or more process supporting devices, and the one or more sensors.

6. The bio-processing system of claim 1, wherein the bio-processing workflow controller further comprises:
a display unit.

7. The bio-processing system of claim 6, wherein the processor is configured to:
generate a workflow configuration user interface using the listing, wherein the workflow configuration user interface comprises controls configured to aid in customizing the arrangement of one or more of the one or more bio-processing units, the one or more process supporting devices, and the one or more sensors;
visualize the workflow configuration user interface on the display unit; and
receive customization inputs via the workflow configuration user interface to customize the arrangement of one or more of the one or more bio-processing units, the one or more process supporting devices, and the one or more sensors; and
create the reconfigurable bio-processing workflow based on the customization inputs.

8. The bio-processing system of claim 1, further comprising a smart switching device operatively coupled to at least one of the one or more bio-processing units and the one or more process supporting devices, wherein the smart switching device is configured to selectively control supply of power to the at least one of the one or more bio-processing units and the one or more process supporting devices.

9. The bio-processing system of claim 8, wherein the smart switching device is configured to selectively control the supply of power to at least one of the one or more bio-processing units and the one or more process supporting devices based on a current signature corresponding to the one or more bio-processing units and the one or more process supporting devices.

10. The bio-processing system of claim 8, wherein the processor is further configured to:
monitor one or more process parameters corresponding to at least one of the one or more bio-processing units, the one or more process supporting devices, and the one or more sensors;
transmit a control command to the smart switching device; and
control the supply of power to at least one of the one or more bio-processing units and the one or more process supporting devices based on the control command.

* * * * *